United States Patent [19]
Appelgren et al.

[11] 4,261,971
[45] Apr. 14, 1981

[54] PHARMACEUTICALLY PREPARATION COMPRISING A CARDIAC GLYCOSIDE IN COMBINATION WITH A POLYMER

[75] Inventors: Curt H. Appelgren, V Frölunda; Conny B. Bogentoft, Kållered, both of Sweden

[73] Assignee: Aktiebolaget Hassle, Molndal, Sweden

[21] Appl. No.: 104,429

[22] Filed: Dec. 17, 1979

[30] Foreign Application Priority Data

Dec. 22, 1978 [SE] Sweden ................................ 7813245

[51] Int. Cl.$^3$ .......................... A61K 9/22; A61K 9/24; A61K 31/705
[52] U.S. Cl. ........................................ 424/21; 424/19; 424/20; 424/32; 424/33; 424/35; 424/182
[58] Field of Search ............................. 424/32, 19–22, 424/33, 182, 35

[56] References Cited

U.S. PATENT DOCUMENTS

| 2,455,790 | 2/1948 | Malm et al. ............................. 424/33 |
| 2,698,822 | 1/1955 | Halpern et al. ....................... 424/182 |
| 2,702,264 | 2/1955 | Klavi ...................................... 424/33 |
| 2,853,420 | 9/1958 | Lowey .................................... 424/35 |
| 2,881,085 | 4/1959 | Endicott et al. ....................... 424/35 |
| 2,921,883 | 1/1960 | Reese et al. ............................ 424/21 |
| 2,928,770 | 3/1960 | Bardani ................................. 424/21 |
| 3,080,294 | 3/1963 | Shepard ................................. 424/21 |
| 3,089,824 | 5/1963 | Wurstor ................................. 424/35 |
| 3,247,066 | 4/1966 | Milosovich ............................. 424/35 |
| 3,325,365 | 6/1967 | Hotko et al. ........................... 424/33 |
| 3,344,029 | 9/1967 | Berger .................................... 424/35 |
| 3,371,015 | 2/1968 | Sjogren et al. ......................... 424/33 |
| 3,400,185 | 9/1968 | Kohnle et al. ......................... 424/35 |
| 3,538,214 | 11/1970 | Polli et al. ............................. 424/35 |
| 3,775,537 | 11/1973 | Lehmann et al. ..................... 424/21 |
| 3,835,221 | 9/1974 | Fulberth et al. ....................... 424/35 |
| 3,954,959 | 5/1976 | Pedersen ................................ 424/21 |
| 3,965,255 | 6/1976 | Bloch et al. ............................ 424/33 |
| 4,083,949 | 4/1978 | Benedikt ................................ 424/35 |
| 4,147,768 | 4/1979 | Shaffer et al. ......................... 424/35 |
| 4,151,273 | 4/1979 | Riegelman et al. ................... 424/78 |

FOREIGN PATENT DOCUMENTS 2651176  5/1977 Fed. Rep. of Germany.

OTHER PUBLICATIONS

Bogentoft et al., Chem. Abstracts 87:73374f (1977).
Bogentoft et al., Chem. Abstracts 90:76495a (1979).

Primary Examiner—Shep K. Rose
Attorney, Agent, or Firm—Graves Brumbaugh

[57] ABSTRACT

A solid pharmaceutical preparation for administration in dosage unit form comprising a therapeutically effective cardiac glycoside, whereby each dosage unit is to comprise a plurality of bodies, each of said bodies having a pharmaceutically inert core and a layer thereon containing the glycoside and a polymer insoluble in gastric juice and soluble in intestinal juice, a process for preparing such preparation and a method of treatment employing the same.

7 Claims, No Drawings

PHARMACEUTICALLY PREPARATION COMPRISING A CARDIAC GLYCOSIDE IN COMBINATION WITH A POLYMER

DESCRIPTION

TECHNICAL FIELD

The present invention is related to a novel pharmaceutical preparation comprising a digitalis glycoside or a similar compound effective in the treatment of cardiac disorders, and a process for producing such preparation, and a method of treatment using such preparation.

An object of the invention is to provide a pharmaceutical preparation in which a cardiac glycoside comprised therein is protected against substantial decomposition in the acid environment of the stomach of a mammal including man, without loss of bioavailability on release and intestinal absorbtion.

A further object is to provide a pharmaceutical preparation giving a sustained or controlled release of a cardiac glycoside comprised therein without loss of bioavailability.

BACKGROUND ART

Digitalis glycosides or cardiac glycosides constitute a class of drugs among which are a few of the oldest drugs in current use. Their main utility is in the treatment of cardiac disorders such as cardiac insufficiency and cardiac arrythmias. The term "cardiac glycosides" as used herein includes therapeutically effective naturally occurring digitalis glycosides and similar compounds of different origin including compounds preparable as semisynthetic derivatives of naturally occurring compounds, irrespective of the manner of obtention thereof. Below, the cardiac glycosides are occasionally referred to as "the active ingredient".

Cardiac glycosides are broken down in an acid environment. This effect is seen especially with digoxin, lanatoside C, digitoxin and proscillaridin.

Thus digoxin is hydrolysed very rapidly in a buffer solution of pH 1 leaving only 10% thereof after exposure for 1 hour. Such decomposition also takes place in vivo; thus it is described that 40% of a given dose may be broken down. As some of the products of hydrolysis have a substantially lower biological activity than has the mother substance, this means that the therapeutical response of a given dose of cardiac glycosides may vary between individuals and between moments of administration depending on how long the preparation stays in the stomach and what pH is prevailing at the time of passage.

It is, however, known in the literature that conventional gastric juice resistant preparations of digitalis glycosides such as tablets provided with a conventional enteric coating give an impaired bioavailability of the glycoside. The fact that digitalis glycosides are difficultly soluble in aqueous media make them further difficult to include in pharmaceutical preparations while obtaining a satisfactory bioavailability.

Digitalis glycosides in general have a narrow therapeutical index, i.e. the dose thereof producing toxic or other undesirable side effects is not much greater than the therapeutically effective dose. Several side effects e.g. nausea and arrythmias encountered in treatment with cardiac glycosides are related to a peak in plasma concentration often occurring a few hours after administration of a dose. For these reasons it is strongly desirable to prepare compositions giving a sustained release of the cardiac glycosides. Bio-pharmaceutical studies have, however, shown that hitherto known sustained release preparations have the drawback of giving an impaired bioavailability of the digitalis glycoside.

DISCLOSURE OF INVENTION

The present invention is related to a pharmaceutical preparation for oral administration in dosage unit form. The pharmaceutical preparation of the invention comprises a cardiac glycoside in combination with a polymer, and is characterized in that said pharmaceutical preparation is in the form of a plurality of small bodies, each body comprising a fraction of a therapeutically effective dosage of the cardiac glycoside, whereby each body has a core made up of pharmaceutically indifferent material, and on said core a layer made up of a composition comprising the cardiac glycoside and an anionic carboxylic polymer being difficultly soluble or insoluble below a given pH value in the interval of pH 4-7.5 but being soluble at a pH above said given value.

Normally each dosage unit contains about 10 to $10^6$ bodies. Preferably the number of bodies is about 200 to 1000. Thus each body of the preparation shall contain a fraction of a therapeutically effective dosage of the cardiac glycoside. The fraction is normally $1.10^{-6}$ to $1.10^{-1}$ times such dosage and preferably $1.10^{-3}$ to $5.10^{-3}$ times such dosage. Among suitable dosage units tablets and capsules are specifically mentioned. Pharmaceutically acceptable additives may be included in the dosage units together with the preparation of the invention. Preparations wherein the solid bodies are in admixture with a liquid medium are also within the scope of the invention.

The cores of the bodies of the preparation may be made up of pharmaceutically indifferent materials in granular or pulverulent form of the type normally used in pharmaceutical preparations, such as sugar, microcrystalline cellulose, starch and waxes. "Pharmaceutically indifferent" means that the materials are indifferent with regard both to the organism treated and the active substance employed. The size of the cores may be sieve fractions between 0.1 and 3.0 mm, preferably between 0.5 and 1.5 mm.

Among active ingredients which may be employed according to the present invention are therapeutically effective compounds containing the ring systems of digitoxigenin.

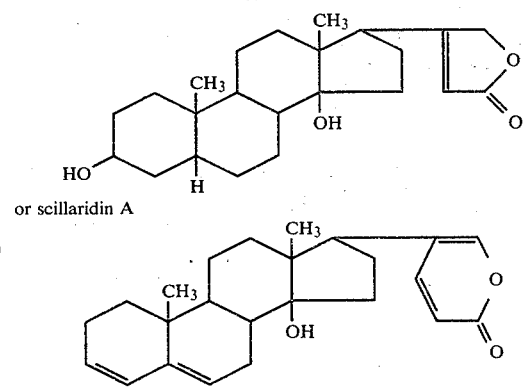

or scillaridin A or derivatives thereof. Of such active ingredients digoxin, digitoxin, lanatoside C, acetyldigoxin, methyl-digoxin, proscillaridin, methylprocillaridin, pentaacetylgitoxin, 16-epigitoxin and actodigin are to be specifically mentioned.

The polymer substance may be selected from the group of anionic carboxylic polymers useful for pharmaceutical purposes and being difficultly soluble at a low pH but being soluble at a higher pH, the pH limit for solubility being in the interval of pH 4 to 7.5, said group comprising celluloseacetate phtalate (CAP)(5-.0-5.5) hydroxypropylmethylcellulose phtalate e.g. a quality sold under the name HP 55 (5.0-5.5), polyvinylacetate phtalate (PVAP) (4.5-5.0) and acrylic acid polymers e.g. partly methyl esterified methacyclic acid polymers such as Eudragit L (6.0) and Eudragit S (7.0), and methylacrylate-methacrylic acid copolymers such as MPM-05 (5.0). Numbers in brackets above are approximate pH limits. These polymers may be used alone or in combination with each other. The polymers may be admixed with plasticizers such as diethyl or dibutyl phtalates, citric acid esters, e.g. acetyltributyl citrate (Citroflex A-4), stearic acid and fatty alcohols such as cetanol. Suitably a polymer is selected which is insoluble or difficultly soluble in gastric juice but soluble in intestinal juice. A preferred polymer is hydroxypropylmethylcellulose phtalate. Further preferred polymers are Eudragit S in combination with hydroxypropylmethylcellulose phtalate or MPM-05.

The relative amounts of core material and material constituting the layer applied thereon may be varied depending i.a. on the properties of the components employed. Preferably the weight of the core relative to the weight of the layer thereon is 1 to between 0.01 and 0.5 most preferably between 0.01 and 0.30.

The bodies prepared preferably have the size of 0.1 to 3 mm. Their shape, partly dependent on the shape of the cores, is preferably spherical or nearly spherical.

According to the present invention it has surprisingly been found possible to obtain protection of the active ingredient by including the active ingredient in admixture with the acid resistant polymer. Among the advantages of the preparations of the present invention are further to be mentioned that they have an improved biological availability as compared to conventional tablets having an enteric coating. The release of the active component in vitro, at a pH over the pH limit selected e.g. the pH of intestinal juice, is rapid with the preparations of the present invention. This is advantageous and accounts in part for the improved bioavailability, however, in vivo a sustained release will occur as the several bodies of the preparation are emptied from the stomach into the small intestine during an extended period of time. The preparation of the invention thereby gives less variation in plasma concentration in patients under continuous treatment than can be obtained with conventional tablets. A further advantage is the improved economy of production that is obtainable, as a batch of the preparation can be prepared in short time, typically 15-20 minutes, while meeting the special demands with preparations of cardiac glycosides.

Another aspect of the present invention is a process for preparing a pharmaceutical preparation for oral administration in dosage unit form.

The invention thus provides a process for preparing a pharmaceutical preparation comprising a cardiac glycoside in combination with a polymer, said process being characterized in that said pharmaceutical preparation is given the form of a plurality of small bodies, each body comprising a fraction of a therapeutically effective dosage of the cardiac glycoside, by providing a large number of cores made up of pharmaceutically indifferent material, with a layer made up of a composition comprising the cardiac glycoside and an anionic carboxylic polymer being difficultly soluble or insoluble below a given pH value in the interval of pH 4-7.5 but being soluble at a pH above said given value, to the formation of such bodies. The layer, which is unitary, is preferably applied by spraying a solution containing the components thereof.

All components of the preparation employed by the process of the invention are as further defined above.

The solvents employed according to the process of the invention are solvents having a sufficient volatility to evaporate under the conditions of application, leaving a layer of the solute on the surface of the core or body prepared. Preferably organic solvents such as alcohols, hydrocarbons and esters are used as well as derivatives thereof, such as chlorinated hydrocarbons. The process of applying the layers may be carried out in an apparatus normally used in the pharmaceutical industry for coating of solid pharmaceutical preparations such as a coating pan or a fluid bed apparatus. The process is normally carried out at ambient conditions, however, temperature and pressure conditions may be varied within broad limits. In a fluid bed spraying process the temperature of the inlet air is suitably 15° to 60° C.

A method of treatment of cardiac disorders employing the pharmaceutical preparation defined above constitutes a further aspect of the invention. The therapeutically effective doses of the cardiac glycosides of the preparations are not greater than those normally prescribed i.e. about 0.05 to 1.5 mg/day for compounds specified herein, subject to variations between different patients. However, it is in many instances possible to employ doses lower than those normally prescribed.

BEST MODE OF CARRYING OUT THE INVENTION

The invention is illustrated by the following examples, of which Example 6 is considered to represent the best mode known at present.

EXAMPLES 1-9

On 500 g of core material, $\phi$0.6-0.7 mm, consisting of 30% starch and 70% sugar a layer was applied by spraying a solution having a composition shown in Table 1 below in a fluid bed apparatus.

The coated granules were analysed according to the so called beaker method (Levy et al, *New England Journal of Medicine*, vol. 262, p. 1053-1058 (1960)). The release of the active ingredient was studied in artificial gastric juice pH 1.0 and phosphate buffer pH 6.5 at 37±0.1° C. Results see Table 2.

TABLE 1

|  |  | Example |  |  |  |  |  |  |  |  |
|---|---|---|---|---|---|---|---|---|---|---|
|  |  | 1 | 2 | 3 | 4 | 5 | 6 | 7 | 8 | 9 |
| Active ingredient |  |  |  |  |  |  |  |  |  |  |
| Digitoxin | (g) | 2.5 |  |  |  |  |  |  |  |  |

TABLE 1-continued

| | | Example | | | | | | | | |
|---|---|---|---|---|---|---|---|---|---|---|
| | | 1 | 2 | 3 | 4 | 5 | 6 | 7 | 8 | 9 |
| Proscillaridin A | (g) | | 2.5 | | | | | | | |
| Digoxin | (g) | | | 2.5 | 1.25 | 1.25 | 1.25 | 1.25 | 1.25 | 1.25 |
| Polymer | | | | | | | | | | |
| HP-55 | (g) | 36 | 36 | 36 | 20 | | | | 20 | 20 |
| Vinnapas B 100 | (g) | | | | 20 | | | | | |
| Eudragit L 100 | (g) | | | | | 20 | | | | |
| Eudragit S 100 | (g) | | | | | 20 | 17.5 | 13 | | 20 |
| CAP | (g) | | | | | | 17.5 | | | |
| PVAP | (g) | | | | | | | 4.5 | | |
| Plasticizer | | | | | | | | | | |
| Cetylalcohol | (g) | 2.5 | 2.5 | 2.5 | 3 | | | | | |
| Stearic acid | (g) | | | | | | 5 | 2.5 | 20 | |
| Solvent | | | | | | | | | | |
| Methylenechloride | (g) | 500 | 500 | 500 | 500 | 500 | 500 | 250 | 500 | 500 |
| Isopropanol | (g) | 300 | 500 | 300 | 300 | 300 | 300 | 150 | 300 | 300 |

TABLE 2

| | % active ingredient released in pH 1.0 after | % active ingredient released in phosphate buffer pH 6.5 after | | |
|---|---|---|---|---|
| Example | 4 h | 10 min | 30 min | 60 min |
| 1 | <1 | 74 | 95 | 100 |
| 2 | 12 | 79 | 102 | |
| 3 | 4 | 99 | 104 | |
| 4 | 7 | 102 | | |
| 5 | <1 | 35 | 88 | 102 |
| 6 | <1 | 64 | 95 | 103 |
| 7 | 1 | 36 | 78 | 94 |
| 8 | 5 | 94 | 100 | |
| 9 | <1 | 52 | 96 | 100 |

Amounts of coated granules prepared according to Examples 6 and 7 corresponding to a dose of 0.38 mg digoxin were filled in hard gelatin capsules size No. 4.

EXAMPLE 10

On 460 g of core material, φ0.2–0.5 mm, consisting of anhydrous lactose, a layer was applied by spraying in a fluid bed apparatus a solution having the following composition:

| Digoxin | 2.5 g |
|---|---|
| Hydroxypropylmethylcellulose phtalate (HP-55) | 8 g |
| Eudragit S 100 | 32 g |
| Methylene chloride | 500 g |
| Isopropanol | 300 g |

Release of digoxin in vitro in percent according to the method referred to in Examples 1–7:

| | Gastric juice | Buffer pH 6.5 |
|---|---|---|
| 10 min | — | 60 |
| 0.5 hours | 1 | 90 |
| 1 hours | 1 | 95 |
| 1.5 hours | — | 97 |
| 2 hours | 2 | 97 |
| 4 hours | 2 | — |

EXAMPLE 11

Example 8 was repeated using 460 g of polyvinylacetate (Vinac ASB 576), φ<0.5 mm, as the core material. Release of digoxin:

| | Gastric juice | Buffer pH 6.5 |
|---|---|---|
| 10 min | — | 32 |
| 0.5 hours | <1 | 69 |
| 1 hours | <1 | 96 |
| 1.5 hours | — | 102 |
| 2 hours | <1 | 102 |
| 4 hours | <1 | — |

We claim:

1. A pharmaceutical preparation comprising a cardiac glycoside in combination with a polymer; characterized in that said pharmaceutical preparation is in the form of a plurality of small bodies, each body comprising a fraction of a therapeutically effective dosage of the cardiac glycoside, whereby each body has a core made up of pharmaceutically indifferent material, and on said core a layer made up of a composition comprising the cardiac glycoside and an anionic carboxylic polymer being difficultly soluble or insoluble below a given pH value in the interval of pH 4–7.5 but being soluble at a pH above said given value.

2. A solid pharmaceutical preparation according to claim 1 characterized in that the layer is a layer applied by spraying a solution of the components thereof.

3. A process for preparing a pharmaceutical preparation comprising a cardiac glycoside in combination with a polymer, characterized in that said pharmaceutical preparation is given the form of a plurality of small bodies, each body comprising a fraction of a therapeutically effective dosage of the cardiac glycoside, by providing a large number of cores made up of pharmaceutically indifferent material, with a layer made up of a composition comprising the cardiac glycoside and an anionic carboxylic polymer being difficultly soluble or insoluble below a given pH value in the interval of pH 4–7.5 but being soluble at a pH above said given value.

4. A process according to claim 3 characterized in that the outer layer is applied by adding a solution of the components thereof.

5. A process according to claim 4 characterized in that the solution is applied by spraying.

6. A process according to claim 4 or 5 characterized in that the outer layer is applied in a fluid bed apparatus.

7. A method of treatment of cardiac disorders comprising administrating to a mammal including man a therapeutically effective dose of the preparation of claim 1.